US012048562B2

(12) United States Patent
Ravuna et al.

(10) Patent No.: US 12,048,562 B2
(45) Date of Patent: Jul. 30, 2024

(54) REDUCING PERCEIVED LATENCY OF CATHETERS

(71) Applicant: BIOSENSE WEBSTER (ISRAEL) LTD., Yokneam (IL)

(72) Inventors: Eliyahu Ravuna, Kiryat Ata (IL); Assaf Govari, Haifa (IL); Tal Haim Bar-on, Kiryat Tivon (IL); Elad Azaria, Ramat Gan (IL); Michael Maydel, Haifa (IL); Alon Ben Natan, Kiryat Bialik (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 400 days.

(21) Appl. No.: 17/462,206

(22) Filed: Aug. 31, 2021

(65) Prior Publication Data
US 2023/0061165 A1    Mar. 2, 2023

(51) Int. Cl.
*A61B 5/00* (2006.01)
*A61B 5/06* (2006.01)
(Continued)

(52) U.S. Cl.
CPC .......... *A61B 5/6852* (2013.01); *A61B 5/062* (2013.01); *A61B 5/367* (2021.01); *A61B 5/7203* (2013.01);
(Continued)

(58) Field of Classification Search
CPC ....... A61B 5/6852; A61B 5/062; A61B 5/367; A61B 2017/00053; A61B 2018/00357;
(Continued)

(56) References Cited

U.S. PATENT DOCUMENTS 5,391,199 A    2/1995   Ben Haim
5,697,377 A    12/1997  Wittkampf
(Continued)

FOREIGN PATENT DOCUMENTS

EP          2514379 A1     10/2012
WO    WO1996005768 A1      2/1996

OTHER PUBLICATIONS

Guiñón [Moving Average and Savitzki-Golay Smoothing Filters Using Mathcad, International Conference on Engineering Education—ICEE 2007]. (Year: 2007).*
(Continued)

*Primary Examiner* — Oommen Jacob

(57) ABSTRACT

In one embodiment, a system includes a catheter, at least one position sensor to provide position signal(s) indicative of a position of a distal end of the catheter over time, a first smoothing filter to provide first filtered position signal(s) responsively to the position signal(s) and a first filtering level, a second smoothing filter to provide second filtered position signal(s) responsively to the position signal(s) and a second filtering level, wherein the second filtering level provides more smoothing than the first filtering level, and processing circuitry to find first and second position coordinates of the distal end responsively to the first and second filtered position signal(s), respectively, generate, and render to a display, an anatomical map of a body part responsively to the second position coordinates, and render a representation of the distal end to the display while showing movement of the distal end responsively to the first position coordinates.

21 Claims, 9 Drawing Sheets

(51) Int. Cl.
*A61B 5/367* (2021.01)
*G06T 5/20* (2006.01)
*G06T 5/70* (2024.01)
*G06T 7/00* (2017.01)
*G16H 40/63* (2018.01)

(52) U.S. Cl.
CPC .............. *A61B 5/725* (2013.01); *A61B 5/743* (2013.01); *G06T 5/20* (2013.01); *G06T 5/70* (2024.01); *G06T 7/0012* (2013.01); *G16H 40/63* (2018.01); *G06T 2207/20182* (2013.01); *G06T 2207/30048* (2013.01)

(58) Field of Classification Search
CPC ........ A61B 5/7203; G06T 2207/30048; G06T 5/002; G06T 2207/20182
See application file for complete search history.

(56) References Cited

U.S. PATENT DOCUMENTS

| | | | |
|---|---|---|---|
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |
| 7,756,576 B2 | 7/2010 | Levin | |
| 7,848,787 B2 | 12/2010 | Osadchy | |
| 7,869,865 B2 | 1/2011 | Govari | |
| 8,165,666 B1* | 4/2012 | Briggs | A61B 5/0036 600/515 |
| 8,647,284 B2 | 2/2014 | Afonso | |
| 10,918,310 B2* | 2/2021 | Cohen | A61B 5/0261 |
| 2002/0065455 A1 | 5/2002 | Ben Haim | |
| 2003/0120150 A1 | 6/2003 | Govari | |
| 2004/0068178 A1 | 4/2004 | Govari | |
| 2006/0257011 A1* | 11/2006 | Li | G06T 11/005 382/131 |
| 2008/0317370 A1* | 12/2008 | Florent | G06V 10/449 382/260 |
| 2009/0262992 A1* | 10/2009 | Markowitz | A61B 5/0536 382/128 |
| 2009/0264738 A1* | 10/2009 | Markowitz | A61B 5/287 600/424 |
| 2012/0157825 A1* | 6/2012 | Koyrakh | A61B 5/063 600/424 |
| 2014/0187905 A1 | 7/2014 | Olson | |
| 2017/0020613 A1 | 1/2017 | Kang | |
| 2017/0323473 A1* | 11/2017 | Wright | A61B 8/08 |
| 2018/0014751 A1 | 1/2018 | Hill | |
| 2023/0061165 A1* | 3/2023 | Ravuna | G06T 7/0012 |
| 2023/0273306 A1* | 8/2023 | Savord | G01S 15/8927 600/457 |

OTHER PUBLICATIONS

Chapter 15, Moving averages from "Scientist & Engineer's Guide to Digital Signal Processing" 1999, (Year: 1999).*

European Search report for corresponding EPA No. 22192828.6 dated Jan. 25, 2023.

* cited by examiner

REDUCING PERCEIVED LATENCY OF CATHETERS

FIELD OF THE INVENTION

The present invention relates to medical systems, and in particular, but not exclusively, to catheter devices.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publication Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser, pulsed field, and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the tip electrode(s) of the ablating catheter, and the reference electrode, flowing through the media between the electrodes it, i.e., blood and tissue. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

SUMMARY

There is provided in accordance with an embodiment of the present invention, a system including a catheter configured to be inserted into a body part of a living subject, and including a distal end, at least one position sensor configured to provide at least one position signal indicative of a position of the distal end of the catheter over time, a display, a first smoothing filter configured to provide at least one first filtered position signal responsively to the at least one position signal and a first filtering level, a second smoothing filter configured to provide at least one second filtered position signal responsively to the at least one position signal and a second filtering level, wherein the second filtering level provides more smoothing than the first filtering level, and processing circuitry configured to find first position coordinates of the distal end responsively to the at least one first filtered position signal, find second position coordinates of the distal end responsively to the at least one second filtered position signal, generate, and render to the display, an anatomical map of the body part responsively to the second position coordinates of the distal end, and render a representation of the distal end of the catheter to the display while showing movement of the distal end of the catheter responsively to the first position coordinates.

Further in accordance with an embodiment of the present invention the first smoothing filter is configured to filter the at least one position signal responsively to the first filtering level providing the at least one first filtered position signal, and the second smoothing filter is configured to filter the at least one position signal responsively to the second filtering level providing the at least one second filtered position signal.

Still further in accordance with an embodiment of the present invention the processing circuitry is configured to compute position coordinates of the distal end responsively to the at least one position signal, and generate at least one position coordinate signal responsively to the computed position coordinates, the first smoothing filter is configured to filter the at least one position coordinate signal responsively to the first filtering level providing the at least one first filtered position signal, and the second smoothing filter is configured to filter the at least one position coordinate signal responsively to the second filtering level providing the at least one second filtered position signal.

Additionally in accordance with an embodiment of the present invention the processing circuitry is configured to render the representation of distal end of the catheter and the anatomical map while showing movement of the catheter in the anatomical map.

Moreover, in accordance with an embodiment of the present invention the processing circuitry is configured to receive a user selected value and set the first filtering level responsively to the user selected value.

Further in accordance with an embodiment of the present invention the first smoothing filter includes a first finite impulse response filter configured to provide the at least one first filtered position signal responsively to the at least one position signal and the first filtering level defined by a first kernel length, and the second smoothing filter includes a second finite impulse response filter configured to provide the at least one second filtered position signal responsively to the at least one position signal and the second filtering level defined by a second kernel length, which is longer than the first kernel length.

Still further in accordance with an embodiment of the present invention the second smoothing filter is configured to provide the at least one second filtered position signal while at least partially preserving peaks included in at least one unfiltered signal input into the second smoothing filter but would be excluded from the at least one second filtered position signal the second filtering level.

Additionally in accordance with an embodiment of the present invention the second smoothing filter is configured to provide the at least one second filtered position signal responsively to a Savitzky-Golay filter.

Moreover in accordance with an embodiment of the present invention the second smoothing filter is configured to detect the peaks in at least one signal smoothed less than the at least one second filtered position signal, and provide the at least one second filtered position signal while at least partially preserving the peaks, included in the at least one unfiltered input signal but would be excluded from the at least one second filtered position signal the second filtering level, responsively to the detected peaks.

Further in accordance with an embodiment of the present invention the second smoothing filter is configured to add the detected peaks to the at least one second filtered position signal.

Still further in accordance with an embodiment of the present invention the second smoothing filter is configured to adjust the at least one second filtered position signal around the added peaks responsively to interpolating between the added peaks and the at least one second filtered position signal.

Additionally in accordance with an embodiment of the present invention the first smoothing filter includes a first finite impulse response filter configured to provide the at least one first filtered position signal responsively to the at least one position signal and the first filtering level defined by a first kernel length, and the second smoothing filter includes a second finite impulse response filter configured to provide the at least one second filtered position signal while at least partially preserving the peaks included in the at least one unfiltered signal input into the second smoothing filter but would be excluded from the at least one second filtered position signal the second filtering level, the second finite impulse filter being configured to apply the second filtering level defined by a second kernel length, which is longer than the first kernel length, to first sections of the at least one unfiltered signal, while applying at least one third filtering level defined by at least one third kernel length to second sections of the at least one unfiltered signal, the at least one third kernel length being shorter than the second kernel length, the second sections being selected to include regions of the detected peaks and regions within a threshold around the detected peaks.

Moreover, in accordance with an embodiment of the present invention the second smoothing filter is configured to gradually reduce the at least one third kernel length from an original value down to a given minimum value when approaching respective locations of the detected peaks, and gradually increase the at least one third kernel length up to the original value when continuing away from the respective locations of the detected peaks.

There is also provided in accordance with another embodiment of the present invention, a method, including providing at least one position signal indicative of a position over time of a distal end of a catheter inserted into a body part of a living subject, providing at least one first filtered position signal responsively to the at least one position signal and a first filtering level, providing at least one second filtered position signal responsively to the at least one position signal and a second filtering level, wherein the second filtering level provides more smoothing than the first filtering level, and finding first position coordinates of the distal end responsively to the at least one first filtered position signal, finding second position coordinates of the distal end responsively to the at least one second filtered position signal, generating, and rendering to a display, an anatomical map of the body part responsively to the second position coordinates of the distal end, and rendering a representation of the distal end of the catheter to the display while showing movement of the distal end of the catheter responsively to the first position coordinates.

Further in accordance with an embodiment of the present invention, the method includes filtering the at least one position signal responsively to the first filtering level providing the at least one first filtered position signal, and filtering the at least one position signal responsively to the second filtering level providing the at least one second filtered position signal.

Still further in accordance with an embodiment of the present invention, the method includes computing position coordinates of the distal end responsively to the at least one position signal, generating at least one position coordinate signal responsively to the computed position coordinates, filtering the at least one position coordinate signal responsively to the first filtering level providing the at least one first filtered position signal, and filtering the at least one position coordinate signal responsively to the second filtering level providing the at least one second filtered position signal.

Additionally in accordance with an embodiment of the present invention, the method includes rendering the representation of distal end of the catheter and the anatomical map while showing movement of the catheter in the anatomical map.

Moreover, in accordance with an embodiment of the present invention, the method includes receiving a user selected value, and setting the first filtering level responsively to the user selected value.

Further in accordance with an embodiment of the present invention the providing the at least one first filtered position signal is performed by a first finite impulse response filter responsively to the at least one position signal and the first filtering level defined by a first kernel length, and the providing the at least one second filtered position signal is performed by a second finite impulse response filter responsively to the at least one position signal and the second filtering level defined by a second kernel length, which is longer than the first kernel length.

Still further in accordance with an embodiment of the present invention the providing the at least one second filtered position signal includes providing the at least one second filtered position signal while at least partially preserving peaks included in at least one unfiltered input signal but would be excluded from the at least one second filtered position signal the second filtering level.

Additionally in accordance with an embodiment of the present invention the providing the at least one second filtered position signal includes providing the at least one second filtered position signal responsively to a Savitzky-Golay filter.

Moreover in accordance with an embodiment of the present invention, the method includes detecting the peaks in at least one signal smoothed less than the at least one second filtered position signal, and wherein the providing the at least one second filtered position signal includes providing the at least one second filtered position signal while at least partially preserving the peaks, included in the at least one unfiltered input signal but would be excluded from the at least one second filtered position signal the second filtering level, responsively to the detected peaks.

Further in accordance with an embodiment of the present invention, the method includes adding the detected peaks to the at least one second filtered position signal.

Still further in accordance with an embodiment of the present invention, the method includes adjusting the at least one second filtered position signal around the added peaks responsively to interpolating between the added peaks and the at least one second filtered position signal.

Additionally in accordance with an embodiment of the present invention the providing the at least one first filtered position signal is performed by a first finite impulse response filter responsively to the at least one position signal and the first filtering level defined by a first kernel length, and the providing the at least one second filtered position signal includes a second finite impulse response filter providing the at least one second filtered position signal while at least partially preserving peaks included in at least one unfiltered input signal but would be excluded from the at least one second filtered position signal the second filtering level, the method further including the second finite impulse filter applying the second filtering level defined by a second kernel length, which is longer than the first kernel length, to first sections of the at least one unfiltered signal, while applying at least one third filtering level defined by at least one third kernel length to second sections of the at least one unfiltered signal, the at least one third kernel length being shorter than the second kernel length, the second sections being selected to include regions of the detected peaks and regions within a threshold around the detected peaks.

Moreover, in accordance with an embodiment of the present invention, the method includes gradually reducing the at least one third kernel length from an original value down to a given minimum value when approaching respective locations of the detected peaks, and gradually increasing the at least one third kernel length up to the original value when continuing away from the respective locations of the detected peaks.

There is also provided in accordance with still another embodiment of the present invention, a software product, including a non-transient computer-readable medium in which program instructions are stored, which instructions, when read by a central processing unit (CPU), cause the CPU to provide at least one first filtered position signal responsively to at least one position signal indicative of a position over time of a distal end of a catheter inserted into a body part of a living subject and a first filtering level, provide at least one second filtered position signal responsively to the at least one position signal and a second filtering level, wherein the second filtering level provides more smoothing than the first filtering level, and find first position coordinates of the distal end responsively to the at least one first filtered position signal, find second position coordinates of the distal end responsively to the at least one second filtered position signal, generate, and render to a display, an anatomical map of the body part responsively to the second position coordinates of the distal end, and render a representation of the distal end of the catheter to the display while showing movement of the distal end of the catheter responsively to the first position coordinates.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
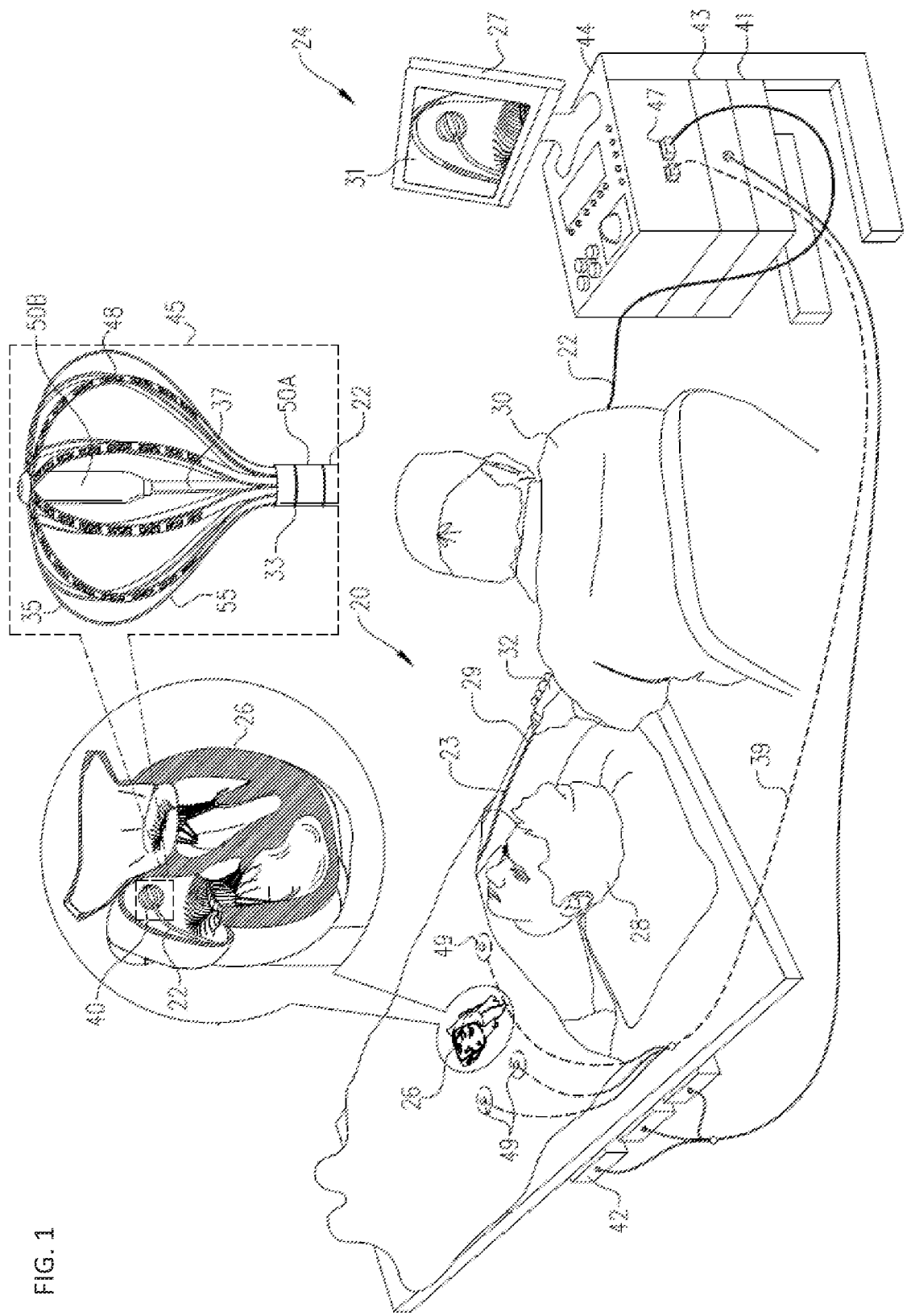
FIG. 1 is a schematic, pictorial illustration of a catheter tracking system constructed and operative in accordance with an exemplary embodiment of the present invention.

Due to effects such as breathing, heartbeat, and other noise, a representation of a tracked catheter viewed on a display will move all the time. This movement is distracting to a physician operating the catheter. Therefore, medical tracking systems such as the CARTO® system, produced by Biosense-Webster, apply a filter (e.g., a low pass filter such as a moving average or Gaussian filter) to position signal(s) used to track movement of the catheter so that the catheter will appear to be stable. However, the price of the stability is latency seen between movement of the catheter by the physician and seeing its movement on the screen.

One solution is to reduce the aggressiveness of the filter leading to less latency seen in the catheter movement. However, the less aggressive filtering also effects the generation of an anatomical map which is also built on the catheter movement. The anatomical map would then be noisy and include artifacts.

Embodiments of the present invention solve the above problems by applying two filtering levels to position signal(s) used to track the movement of the catheter. One filtering level is an aggressive filtering used by an electrophysiological (EP) sub-system which generates anatomical maps, and one filtering level is a non-aggressive (or less aggressive) filtering used by a catheter movement tracking sub-system to show real-time movement of the catheter. In this manner, the representation of the catheter seen on the display has less latency, while the anatomical map in which the catheter is moving, is generated based on suitably filtered position signal(s). The user (e.g., physician) may be given an option to adjust the aggressiveness of the filtering level used to show real-time time movement of the catheter.

In some embodiments, the aggressive and non-aggressive filters may be implemented using finite impulse response (FIR) low-pass filters with the aggressive filter having a longer kernel than the non-aggressive filter.

In some cases, the above solution may introduce a problem. The aggressive filter generally filters peaks from the position signal(s) while the non-aggressive filter leaves more of the peaks in the signal(s). Therefore, the user may be able to see to which 'peak location' the catheter arrived in reality but because the anatomical map is built using signal(s) filtered by the aggressive filter, the map may not extend to the 'peak location' leading to a discrepancy between the motion of the catheter, as seen on the display, and the map built by the EP system. For example, it may appear that the catheter is moving through the wall of the body part (e.g., the heart). One naïve solution is to use the non-aggressive filter for map building purposes too. However, this would incur too much noise to the resulting anatomical map as mentioned previously.

Embodiments of the present invention solve the above problems by filtering the position signal(s) used by the EP sub-system using the aggressive filter with peak preservation so that peaks found in the non-filtered or non-aggressively filtered signal(s) are at least partially preserved in the aggressively filtered signal(s).

In some embodiments, a Savitzky-Golay filter may be used to preserve peaks in the aggressively filtered signal(s). In some embodiments, the non-aggressively filtered signal(s) may also be provided using a suitably configured Savitzky-Golay filter.

In some embodiments, peaks may be detected in the non-filtered or non-aggressively filtered signal(s), and the aggressively filtered signal(s) may then be processed according to the detected peaks to affect peak preservation in the aggressively filtered signal(s). In some embodiments, the detected peaks may be added to the aggressively filtered signal(s) and optionally the aggressively filtered signal(s) may be amended using interpolation to interpolate between the added peaks and points in the existing signal(s) either side of the added peaks.

In some embodiments, the aggressive and non-aggressive filters may be designed as FIR low-pass filters, with the aggressive filter having a longer kernel than the non-aggressive filter. The non-aggressive filter may be used to detect peaks as the kernel of the non-aggressive filter is short enough for the peaks to remain in the signal(s). Whenever a peak is detected by the non-aggressive filter, the peak may be "implanted" into the results of the aggressive filter, causing the aggressive filter to give the same results as the non-aggressive filter around the peaks. But outside the peaks, the aggressive filter performs a strong smoothing. In this context, "around the peaks" can be defined as +/−N samples around each peak. So, +/−N samples around each peak may be copied as-is from the results of the non-aggressive filter to the results of the aggressive filter. Alternatively, +/−N samples around the peaks may be interpolated, in a way to arrive to the same peak.

In disclosed embodiments, a FIR filter may be used as the aggressive filter. At every peak detected by the non-aggressive filter, the kernel length of the aggressive filter may be gradually shortened from around the peaks towards the peaks. For example, if the length of the kernel of the aggressive filter is generally 7, the kernel length of the aggressive filter is gradually reduced around each detected peak from 7 to 5, then to 3, then to 1 at the detected peak. A kernel length of 1 practically means copying the raw sample as-is. This results in a smoother transition between the signal of the aggressive filter and the peak "copied" from the non-aggressive filter.

System Description

Reference is now made to FIG. 1, which is a schematic, pictorial illustration of a catheter tracking system 20, in accordance with an exemplary embodiment of the present invention. The system 20 includes a catheter 40 configured to be inserted into a body part of a living subject (e.g., a patient 28). A physician 30 navigates the catheter 40 (for example, a basket catheter produced by Biosense Webster, Inc. of Irvine, CA, USA), seen in detail in inset 45, to a target location in a heart 26 of the patient 28, by manipulating a deflectable segment of an insertion tube 22 of the catheter 40, using a manipulator 32 near a proximal end 29 of the insertion tube 22, and/or deflection from a sheath 23. In the pictured embodiment, physician 30 uses catheter 40 to perform electro-anatomical mapping of a cardiac chamber.

The catheter 40 includes a distal end 33. The distal end 33 of the catheter 40 includes an assembly 35 (e.g., a basket assembly as shown in FIG. 1 or a balloon assembly or any suitable distal end assembly, e.g., grid, flexible splines or a focal catheter) on which at least one (e.g., multiple) electrode(s) 48 (only some labeled for the sake of simplicity) are disposed. The assembly 35 is disposed distally to the insertion tube 22 and may be connected to the insertion tube 22 via a coupling member of the insertion tube 22 at the distal end 33. The coupling member of the insertion tube 22 may be formed as an integral part of the rest of the insertion tube 22 or as a separate element which connects with the rest of the insertion tube 22.

The assembly 35 further comprises multiple flexible strips 55 (only two labeled for the sake of simplicity), to each of which are coupled the electrodes 48. The assembly 35 may include any suitable number of electrodes 48. In some embodiments, the assembly 35 may include ten flexible strips 55 and 120 electrodes, with twelve electrodes disposed on each flexible strip 55.

The catheter 40 includes a pusher 37. The pusher 37 is typically a tube that is disposed in a lumen of the insertion tube 22 and spans from the proximal end 29 to the distal end 33 of the insertion tube 22. A distal end of the pusher 37 is connected to distal ends of the flexible strips 55, typically via a coupling member of the pusher 37. The coupling member of the pusher 37 may be formed as an integral part of the rest of the pusher 37 or as a separate element which connects with the rest of the pusher 37. The distal end of the insertion tube 22 is connected to proximal ends of the flexible strips 55, typically via the coupling member of the distal end 33. The pusher 37 is generally controlled via the manipulator 32 to deploy the assembly 35 and change an ellipticity of the assembly 35 according to the longitudinal displacement of the pusher 37 with respect to the insertion tube 22. The actual basket assembly 35 structure may vary. For example, flexible strips 55 may be made of a printed circuit board (PCB), or of a shape-memory alloy, or any suitable material.

Embodiments described herein refer mainly to a basket distal-end assembly 35, purely by way of example. In alternative embodiments, the disclosed techniques can be used with a catheter having a balloon-based distal-end assembly or of any other suitable type of distal-end assembly.

Catheter 40 is inserted in a folded configuration, through sheath 23, and only after the catheter 40 exits sheath 23 is catheter 40 able to change shape by retracting pusher 37. By containing catheter 40 in a folded configuration, sheath 23 also serves to minimize vascular trauma on its way to the target location.

The distal end 33 of the catheter 40 comprises magnetic coil sensors 50A and 50B. The magnetic coil sensor 50A is shown in inset 45 at the distal edge of insertion tube 22 (i.e., at the proximal edge of basket assembly 35). The sensor 50A may be a Single-Axis Sensor (SAS), or a Double-Axis Sensor (DAS) or a Triple-Axis Sensor (TAS). Similarly, the sensor 50B may be a SAS, DAS, or TAS. Magnetic coil sensors 50A and 50B and electrodes 48 are connected by wires running through insertion tube 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between sensors 50A and 50B. Patient 28 is placed in a magnetic field generated by a pad containing multiple magnetic field generator coils 42, which are driven by a unit 43. The magnetic field generator coils 42 are configured to generate respective alternating magnetic fields, having respective different frequencies, into a region where a body-part (e.g., the heart 26) of a living subject (e.g., the patient 28) is located. The magnetic coil sensors 50A and 50B are configured to output electrical signals responsively to detecting the respective magnetic fields. For example, if there are nine magnetic field generator coils 42 generating nine respective different alternating magnetic fields with nine respective different frequencies, the electrical signals output by the magnetic coil sensors 50 will include components of the nine different frequency alternating magnetic fields. The magnitude of each of the magnetic fields varies with distance from the respective magnetic field generator coils 42 such that the location of the magnetic coil sensors 50 may be determined from the magnetic fields sensed by the magnetic coil sensors 50. Therefore, the transmitted alternating magnetic fields generate the electrical signals in sensors 50A and 50B, so that the electrical signals are indicative of position and orientation of the magnetic coil sensors 50.

The generated signals are transmitted to console 24 and become corresponding electrical inputs to processing circuitry 41. The processing circuitry 41 may use the signals to compute: the elongation of the basket assembly 35, in order to estimate basket ellipticity and elongation/retraction state from the calculated distance between sensors 50A and 50B; and compute a relative orientation between the axes of the sensors 50A and 50B to estimate a shape of the expandable distal end assembly 35 (e.g., a basket shape) responsively to the relative orientation, as described in more detail below.

The bow of the flexible strips 55 and/or the positions of the electrodes 48 (or other features) on the flexible strips 55 with respect to a fixed point on the catheter 40 (such as the distal tip of the insertion tube 22) may be measured for various distances between the magnetic sensors 50A, 50B and for various relative orientation angles between the magnetic sensors 50A, 50B. For example, the positions of the electrodes 48 with respect to the fixed point on the catheter 40 may be measured for every 0.2 mm movement of the pusher 37 with respect to the insertion tube 22 and for every 1 degree of relative orientation between the magnetic sensors 50A, 50B (up to a maximum sideways movement of the assembly 35). At each different distance/relative-orientation combination, the computed distance and computed relative orientation angle between the magnetic sensors 50A, 50B is recorded along with the position data of the electrodes 48. This data may then be used to estimate the bow of the flexible strips 55 and/or the positions of the electrodes 48 (or other features) on the flexible strips 55 with respect to a fixed point on the catheter 40 (such as the distal tip of the insertion tube 22) responsively to the computed distance and relative orientation angle between the magnetic sensors 50A, 50B.

Additionally, or alternatively, the bow of the flexible strips 55 may be estimated based on the following assumptions: (a) each of the flexible strips 55 is of a fixed and known length; (b) each of the flexible strips 55 is connected to the pusher 37 via a coupler, with the distal ends of the flexible strips 55 being substantially perpendicular (within an error of plus or minus 10 degrees) to the longitudinal axis of the insertion tube 22; (c) each of the flexible strips 55 is connected to the insertion tube 22 via a coupler, which couples the proximal ends of the flexible strips 55 to the insertion tube 22, substantially parallel (within an error of plus or minus 10 degrees) to the longitudinal axis of the insertion tube 22. Based on the above assumptions (a)-(c), and the computed positions of the couplers based on the computed positions of the magnetic sensors 50A, 50B, the bow of each of the flexible strips 55 may be computed using a third-degree polynomial. In some embodiments, the bow of the flexible strips 55 and/or the positions of the electrodes 48 (or other features) on the flexible strips 55 with respect to a fixed point on the catheter 40 (such as the distal tip of the insertion tube 22) may be computed based on the computed distance and orientation between the magnetic sensors 50A, 50B and a model of the catheter 40 which provides the bow of the flexible strips 55 and/or the positions of the electrodes 48 for the computed distance based on the mechanical properties and dimensions of the flexible strips 55.

A method of position and/or direction sensing using external magnetic fields and magnetic coil sensors, such as sensors 50A and 50B, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1.

In some embodiments, the processing circuitry 41 uses position-signals received from the electrodes 48 or body surface electrodes 49, and the magnetic sensor 50 to estimate a position of the assembly 35 inside a body part, such as inside a cardiac chamber. In some embodiments, the processing circuitry 41 correlates the position signals received from the electrodes 48, 49 with previously acquired magnetic location-calibrated position signals, to estimate the position of the assembly 35 inside the body part. The position coordinates of the electrodes 48 may be determined by the processing circuitry 41 based on, among other inputs, measured impedances, voltages or on proportions of currents distribution, between the electrodes 48 and the body surface electrodes 49.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publication Nos. 2002/0065455 A1, 2003/0120150 A1 and 2004/0068178 A1.

The Carto®3 system applies Active Current Location (ACL) which is a hybrid current-distribution and magnetic-based position-tracking technology. In some embodiments, using ACL, the processing circuitry 41 estimates the positions of the electrodes 48. In some embodiments, the signals received from the electrodes 48, 49 are correlated with a current-to-position matrix (CPM) which maps current distribution ratios (or another electrical value) with a position that was previously acquired from magnetic location-calibrated position signals. The current distribution ratios are based on measurements of the body surface electrodes 49 of current flowing from the electrodes 48 to the body surface electrodes 49.

In some embodiments, to visualize catheters which do not include a magnetic sensor, the processing circuitry 41 may apply an electrical signal-based method, referred to as Independent Current Location (ICL) technology. In ICL, the processing circuitry 41 calculates a local scaling factor for each voxel of the volume in which catheters are visualized. The factor is determined using a catheter with multiple electrodes having a known spatial relationship, such as a lasso-shaped catheter. However, although yielding accurate local scaling (e.g., over several millimeters), ICL is less accurate when applied to a volume of a whole heart chamber, whose size is in the order of centimeters. The ICL method, in which positions are calculated based on current distribution proportions can have errors and may yield a distorted shape of the assembly 35, due to the non-linear nature of the current-based ICL space. In some embodiments, the processing circuitry 41 may apply the disclosed ICL method to scale ICL space and the assembly 35 shape into a correct one, based on known smaller scale distances between electrodes of a lasso-shaped catheter, for example, as well as based on larger scale distances, themselves based on the known distance between the electrodes 48 at the ends of the assembly 35.

Processing circuitry 41, typically part of a general-purpose computer, is further connected via a suitable front end and interface circuits 44, to receive signals from body surface-electrodes 49. Processing circuitry 41 is connected to surface-electrodes 49 by wires running through a cable 39 to the chest of patient 28. The catheter 40 includes a connector 47 disposed at the proximal end 29 of the insertion tube 22 for coupling to the processing circuitry 41.

In some embodiments, processing circuitry 41 renders to a display 27, a representation 31 of at least a part of the catheter 40 and a body-part, (e.g., from a mapping process or from a scan (e.g., CT or MRI) of the body-part previously registered with the system 20), responsively to computed position coordinates of the insertion tube 22 and the flexible strips 55.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2:
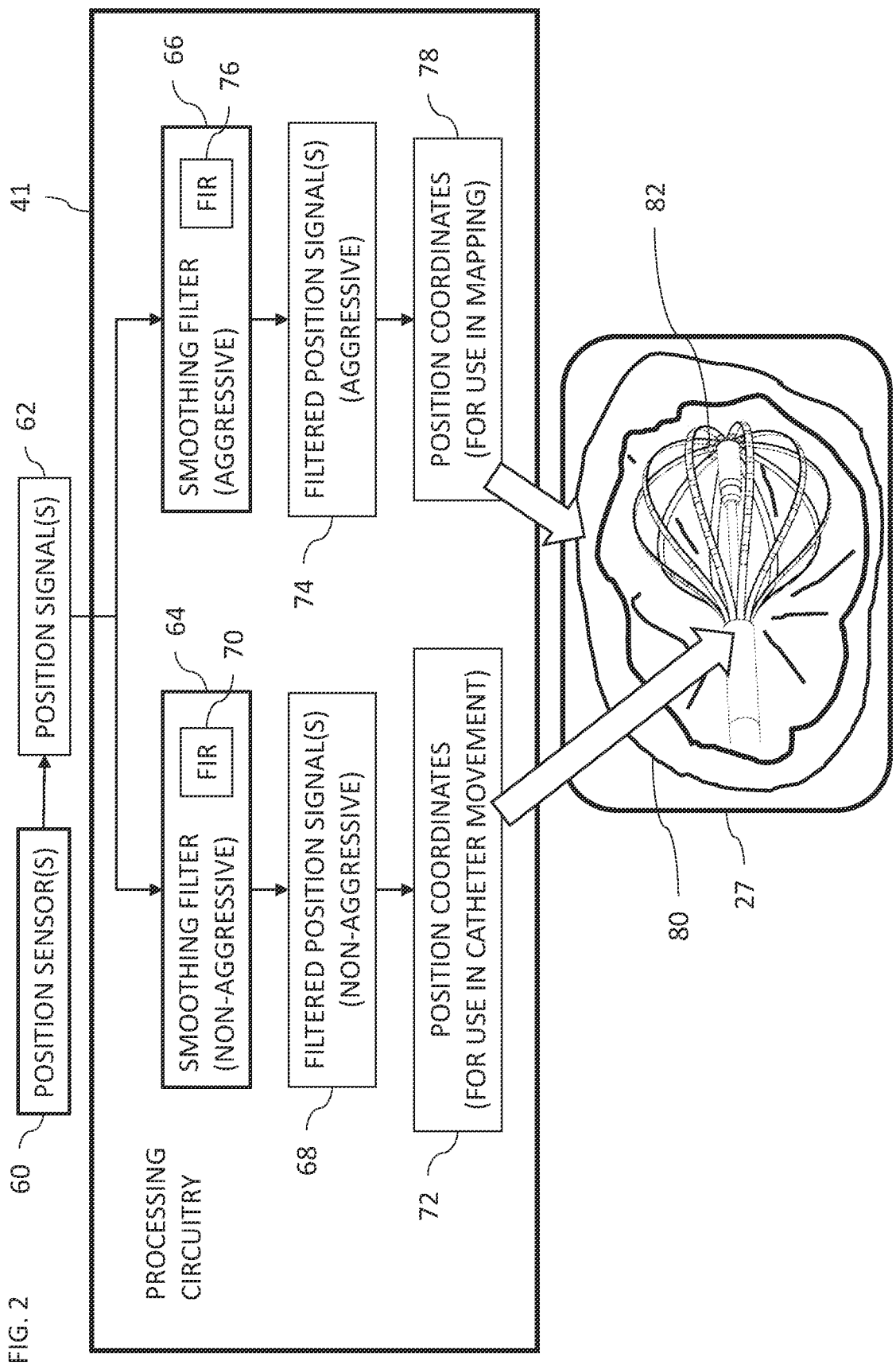
FIG. 2 is a partly pictorial, partly block diagram view of signal processing and rendering to a display in the system of FIG. 1.
Figure 3:
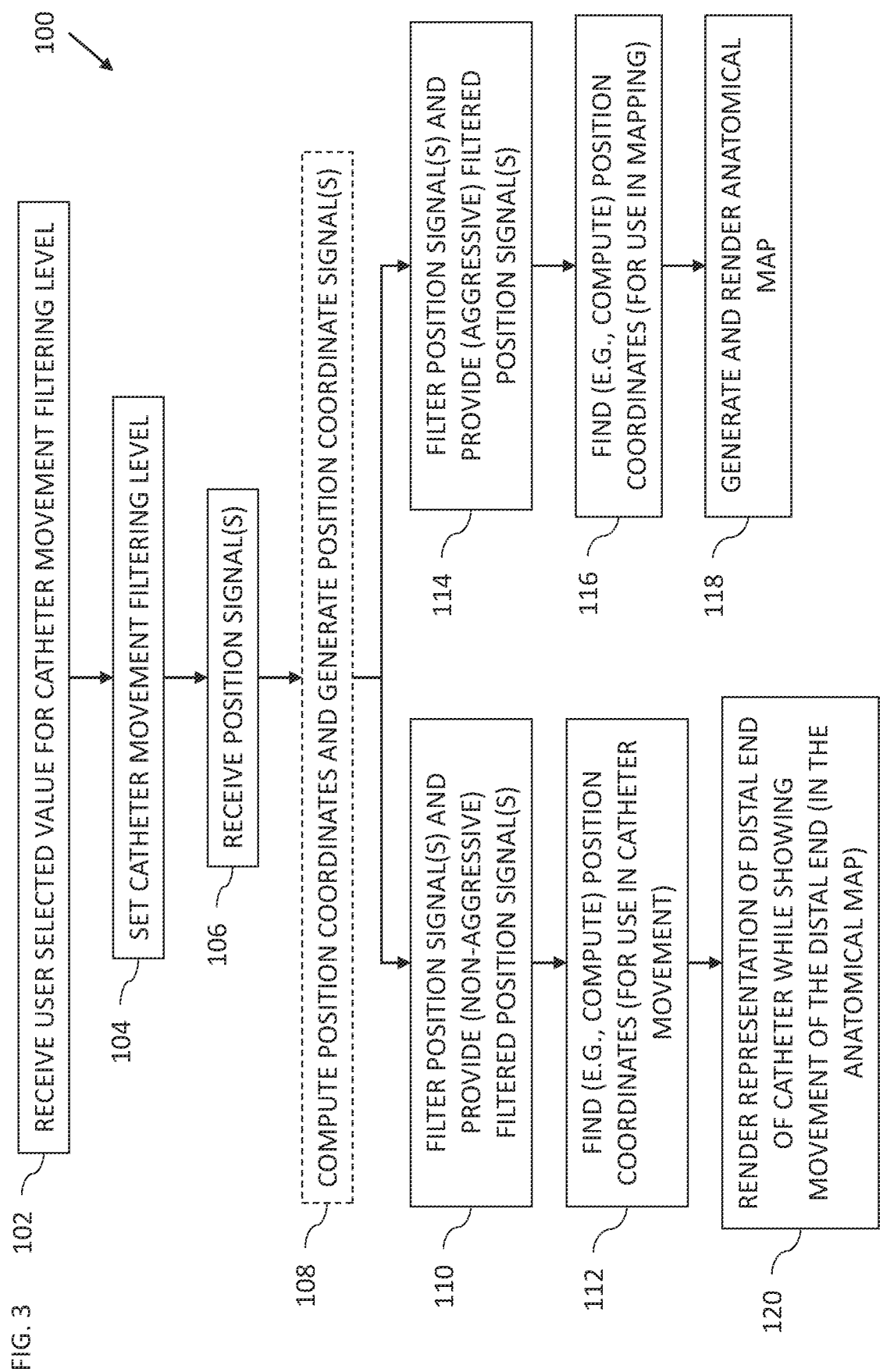
FIG. 3. is a flowchart including steps in a method of operation of the system of FIG. 1.

Reference is now made to FIGS. 2 and 3. FIG. 2 is a partly pictorial, partly block diagram view of signal processing and rendering to display 27 in the system 20 of FIG. 1. FIG. 3 is a flowchart 100 including steps in a method of operation of the system 20 of FIG. 1.

The processing circuitry 41 is configured to receive (block 102) a user selected value for setting a filtering level to be used to control movement of the display of the catheter 40. The processing circuitry 41 is configured to set (block 104) a first filtering level responsively to the user selected value.

The catheter tracking system 20 includes at least one position sensor 60 configured to provide at least one position signal 62 indicative of a position of the distal end 33 of the catheter 40 over time. The position sensor(s) 60 may include any one or more of: the electrode(s) 48, the magnetic coil sensor(s) 50; and/or the body surface electrodes 49. The processing circuitry 41 is configured to receive (block 106) the position signal(s) 62 from the position sensor 60.

In some embodiments, the processing circuitry 41 is configured to: compute (block 108) position coordinates of the distal end 33 responsively to the position signal(s) 62; and generate at least one position coordinate signal responsively to the computed position coordinates. The position coordinate signals are then filtered as described below. In some embodiments, the position signal(s) 62 are filtered and then position coordinates are derived from the filtered position signals as described below in the steps of blocks 112 and 116.

The processing circuitry 41 may include a non-aggressive smoothing filter 64 and an aggressive smoothing filter 66. The terms "non-aggressive" and "aggressive" are relative terms with the non-aggressive smoothing filter 64 being less aggressive (i.e., providing less smoothing) than the aggressive smoothing filter 66.

The smoothing filter 64 is configured to provide (block 110) at least one non-aggressively filtered position signal 68 responsively to the position signal(s) 62 and the first filtering level. In some embodiments, the smoothing filter 64 is configured to filter the position signal(s) 62 responsively to the first filtering level providing the non-aggressively filtered position signal(s) 68. In other embodiments, the smoothing filter 64 is configured to filter the position coordinate signal(s) generated in the step of block 108 responsively to the first filtering level providing the non-aggressively filtered position signal(s) 68.

In some embodiments, the smoothing filter 64 includes a finite impulse response filter 70 configured to provide the non-aggressively filtered position signal(s) 68 responsively to the position signal(s) 62 (or the position coordinate signal(s) generated in the step of block 108) and the first filtering level defined by a first kernel length.

The processing circuitry 41 is configured to find (e.g., compute) (block 112) position coordinates 72 (for use in display of catheter movement) of the distal end 33, responsively to the non-aggressively filtered position signal(s) 68.

The smoothing filter 66 is configured to provide (block 114) at least one aggressively filtered position signal 74 responsively to the position signal(s) 62 and a second filtering level. The second filtering level provides more smoothing than the first filtering level. In some embodiments, the smoothing filter 66 is configured to filter the position signal(s) 62 responsively to the second filtering level providing the aggressively filtered position signal(s) 74. In other embodiments, the smoothing filter 66 is configured to filter the position coordinate signal(s) generated in the step of block 108 responsively to the second filtering level providing the aggressively filtered position signal(s) 74.

In some embodiments, the smoothing filter 66 includes a finite impulse response filter 76 configured to provide the aggressively filtered position signal(s) 74 responsively to the position signal(s) 62 (or the position coordinate signal(s)

generated in the step of block 108) and the second filtering level defined by a second kernel length, which is longer than the first kernel length (used by the finite impulse response filter 70).

The processing circuitry 41 is configured to find (e.g., compute) (block 116) position coordinates 78 (for use in mapping) of the distal end 33 responsively to the aggressively filtered position signal(s) 74. The processing circuitry 41 is configured to generate, and render (block 118) to the display 27, an anatomical map 80 of the body part responsively to the position coordinates 78 of the distal end 33. The anatomical map 80 may be generated using any suitable map generation method, for example, but not limited to, Fast Anatomical Mapping (FAM). FAM is described in U.S. Pat. No. 10,918,310 to Cohen, et al. In FAM, a smooth shell is generated around a three-dimensional (3D) cloud of data points, such as a cloud of computed electrode positions of the electrodes 48.

The processing circuitry 41 is configured to render (block 120) a representation 82 of the distal end 33 of the catheter 40 to the display 27 while showing movement of the distal end 33 of the catheter 40 responsively to the position coordinates 72. In some embodiments, the processing circuitry 41 is configured to render the representation 82 of distal end 33 of the catheter 40 and the anatomical map 80 while showing movement of the catheter 40 in the anatomical map 80.

Figure 4:
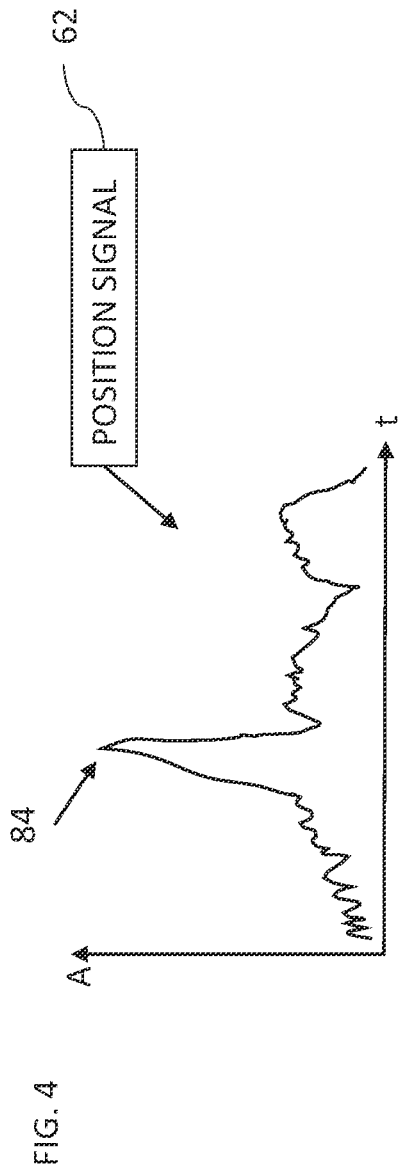
FIGS. 4-6 are example signals generated in the system of FIG. 1.
Figure 6:
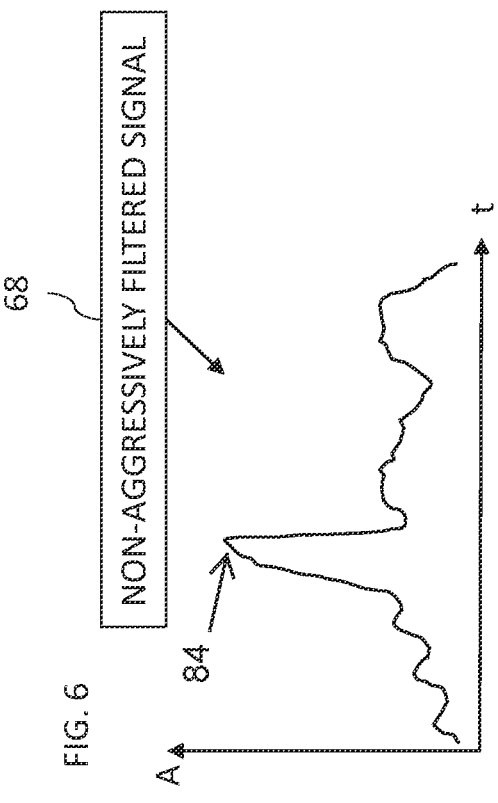
Figure 5:
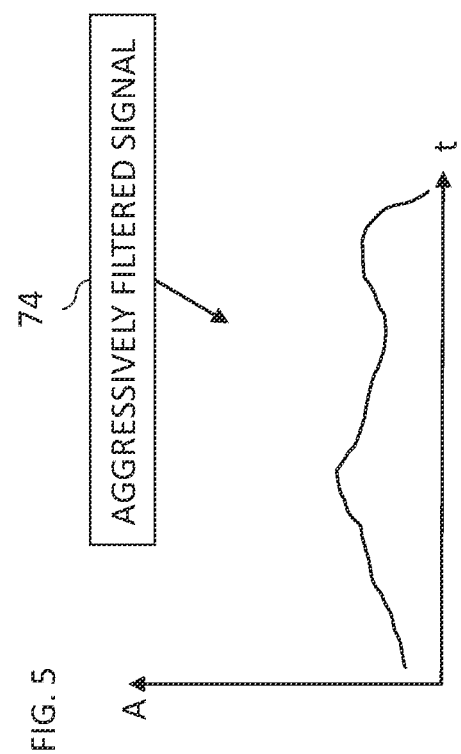

Reference is now made to FIGS. 4-6, which are example signals generated in the system 20 of FIG. 1. FIG. 4 shows an example of one of the position signals 62 and includes a peak 84. FIG. 5 shows an example of one of the aggressively filtered position signals 74. The aggressively filtered position signal 74 of FIG. 5 is smooth but lacks the peak 84 shown in FIG. 4. FIG. 6 shows an example of one of the non-aggressively filtered position signals 68, which is not as smoothed as the aggressively filtered position signal 74 of FIG. 5 but includes the peak 84 of FIG. 4. As previously mentioned, the aggressive smoothing filter 66 generally filters peaks from the position signal(s) 62 while the non-aggressive filter 64 leaves more of the peaks in the signal(s). Therefore, the user may be able to see to which 'peak location' the catheter 40 arrived in reality but because the anatomical map 80 is built using signal(s) filtered by the aggressive filter 66, the map 80 may not extend to the 'peak location' leading to a discrepancy between the motion of the catheter 40 as seen on the display 27, and the map 80 built by the EP system. For example, it may appear that the catheter 40 is moving through the wall of the body part (e.g., heart).

One naïve solution is to use the non-aggressive filter 64 for map building purposes too. However, this would incur too much noise to the resulting anatomical map as mentioned previously. Embodiments of the present invention solve the above problems by filtering the position signal(s) used by the EP sub-system using the aggressive filter 66 with peak preservation so that peaks found in the non-filtered or non-aggressively filtered signal(s) 68 are at least partially preserved in the aggressively filtered signal(s) 74.

Figure 7:
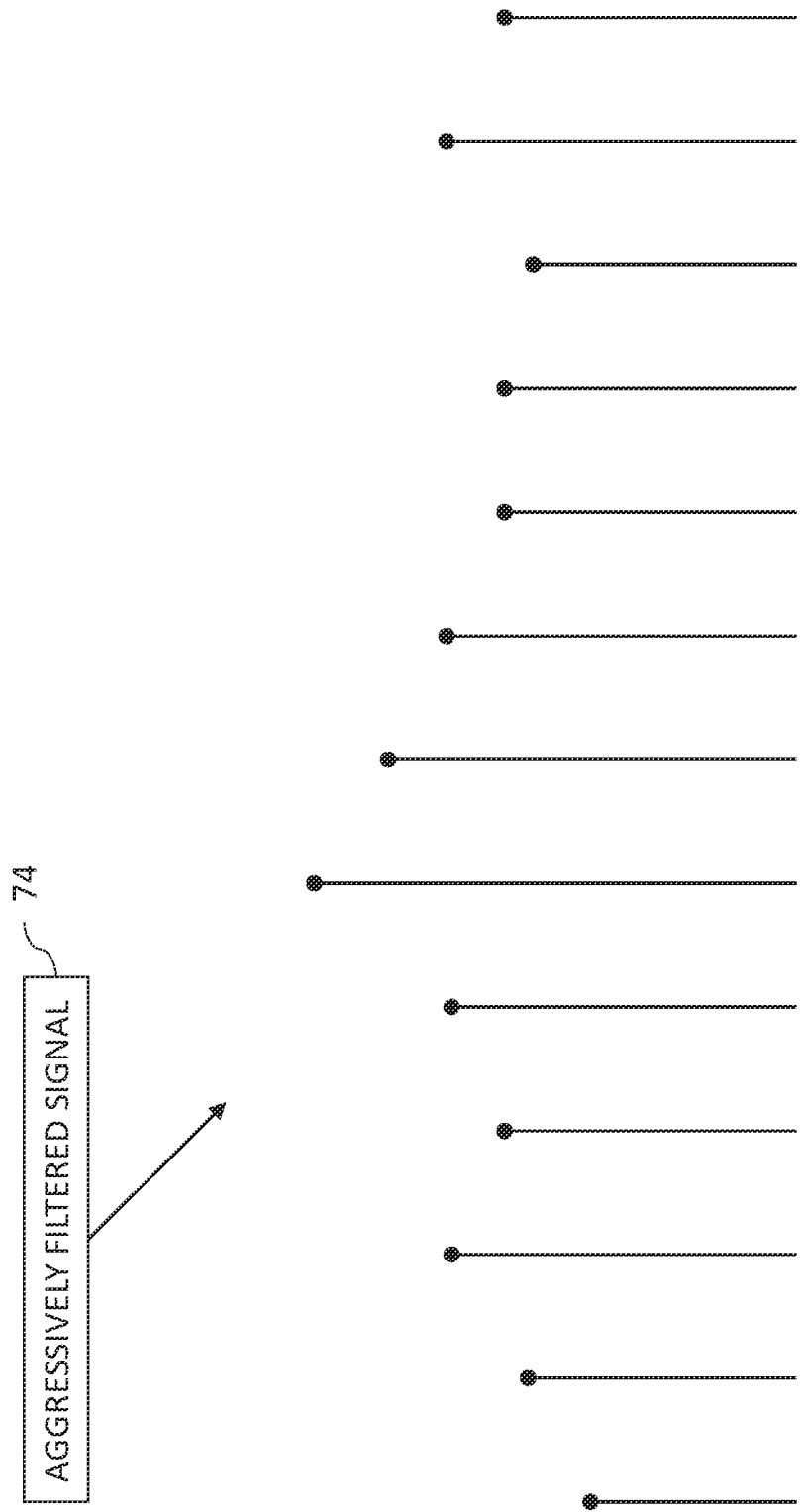
FIG. 7 is an example of a more aggressively filtered position signal generated in the system of FIG. 1.
Figure 8:
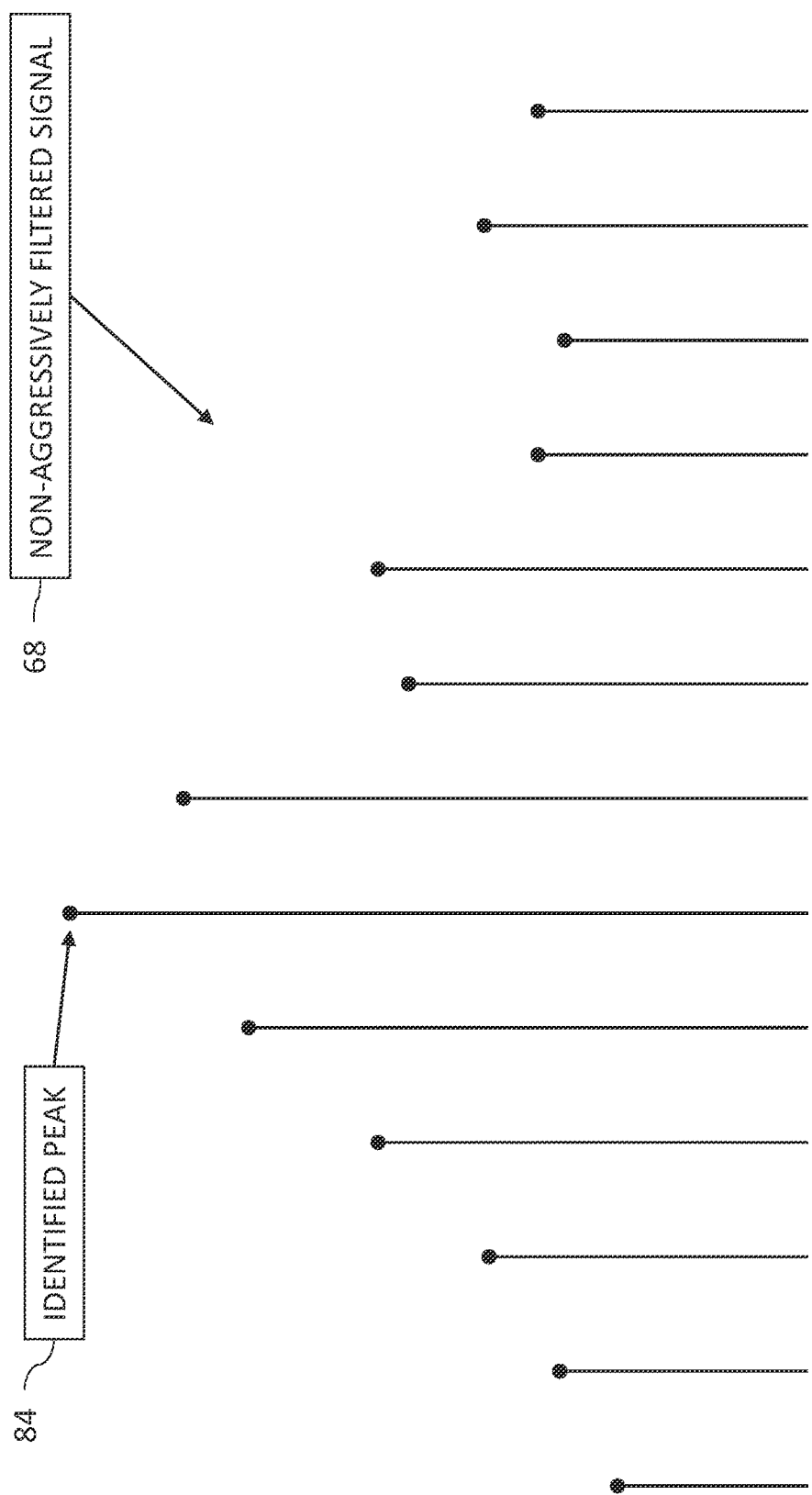
FIG. 8 is an example of a less aggressively filtered position signal generated in the system of FIG. 1.

Reference is now made to FIGS. 7 and 8. FIG. 7 shows an example of an aggressively filtered position signal 74 generated in the system 20 of FIG. 1. FIG. 8 shows an example of a non-aggressively filtered position signal 68 generated in the system 20 of FIG. 1. The non-aggressively filtered position signal 68 includes the peak 84. The peak 84 may be identified in the non-aggressively filtered position signal 68 and then added to the aggressively filtered position signal(s) 74 as described in more detail with reference to FIG. 9 or FIG. 10. The small circles on top of the vertical lines in FIGS. 7 and 8 represent the amplitude of the signals 68, 74 at respective times with increasing time going from left to right.

A peak may be defined as a local maximum whose amplitude is: at least $X_{RELATIVE}\%$ above the $P^{th}$ percentile of the surroundings; and/or at least $X_{RELATIVE}\%$ above the average of the surroundings; and/or at least $X_{ABSOLUTE}$ millivolts above the $P^{th}$ percentile of the surroundings; and/or at least $X_{ABSOLUTE}$ millivolts above the average of the surroundings.

The surroundings may be defined as +/−N neighboring samples. N may be any suitable value. For example, assuming that the signal is sampled at 60 samples per second, N may be chosen as 30. In this specific example, a neighborhood of +/−30 samples results in a sliding filtering window of a 1 second width.

$X_{RELATIVE}\%$ may have any suitable value, for example, 30%. $X_{ABSOLUTE}$ millivolts may have any suitable value depending upon the voltage output of the position sensor(s) 60, for example 0.1 millivolts.

P may have any suitable value, for example, 50, 75 or 90. When P is 50, $P^{th}$ percentile is the median. When P is 75, $P^{th}$ percentile is the $3^{rd}$ quartile. Setting P to 90 may be appropriate to approximate the maximum value without taking the outliers.

In some embodiments, detecting peaks may be performed solely using an $X_{RELATIVE}$ percentage cutoff thereby removing the need to define an arbitrary $X_{ABSOLUTE}$ limit. However, detecting peaks based solely on an $X_{RELATIVE}$ percentage, without any $X_{ABSOLUTE}$ limit, may detect false peaks, for example, noise in an almost zero sample region of a signal may look like a peak. For example, when all values in the signal are almost zero, a human eye can immediately see that there is no peak. However, even when all values are almost zero, some numbers may still be much larger than its surroundings in relative terms. In this case, a system that analyzes the height of the peaks in terms of a $X_{RELATIVE}$ percentage will detect a false peak. "AND"ing (i.e., combining) the $X_{RELATIVE}$ condition with some $X_{ABSOLUTE}$ condition has the advantage of reducing the false detection of peaks, especially in noisy signals composed of low values. For example, a peak may be defined as a sample that is both 30% larger than its surroundings ($X_{RELATIVE}=30\%$), and at least 0.1 millivolts higher than its surroundings ($X_{ABSOLUTE}=0.1$ millivolts) at the same time.

The system may search for peaks either in the signal filtered with the non-aggressive filter, or in the signal filtered with the aggressive filter, or in the raw signal (e.g., position signal(s) 62).

Figure 9:
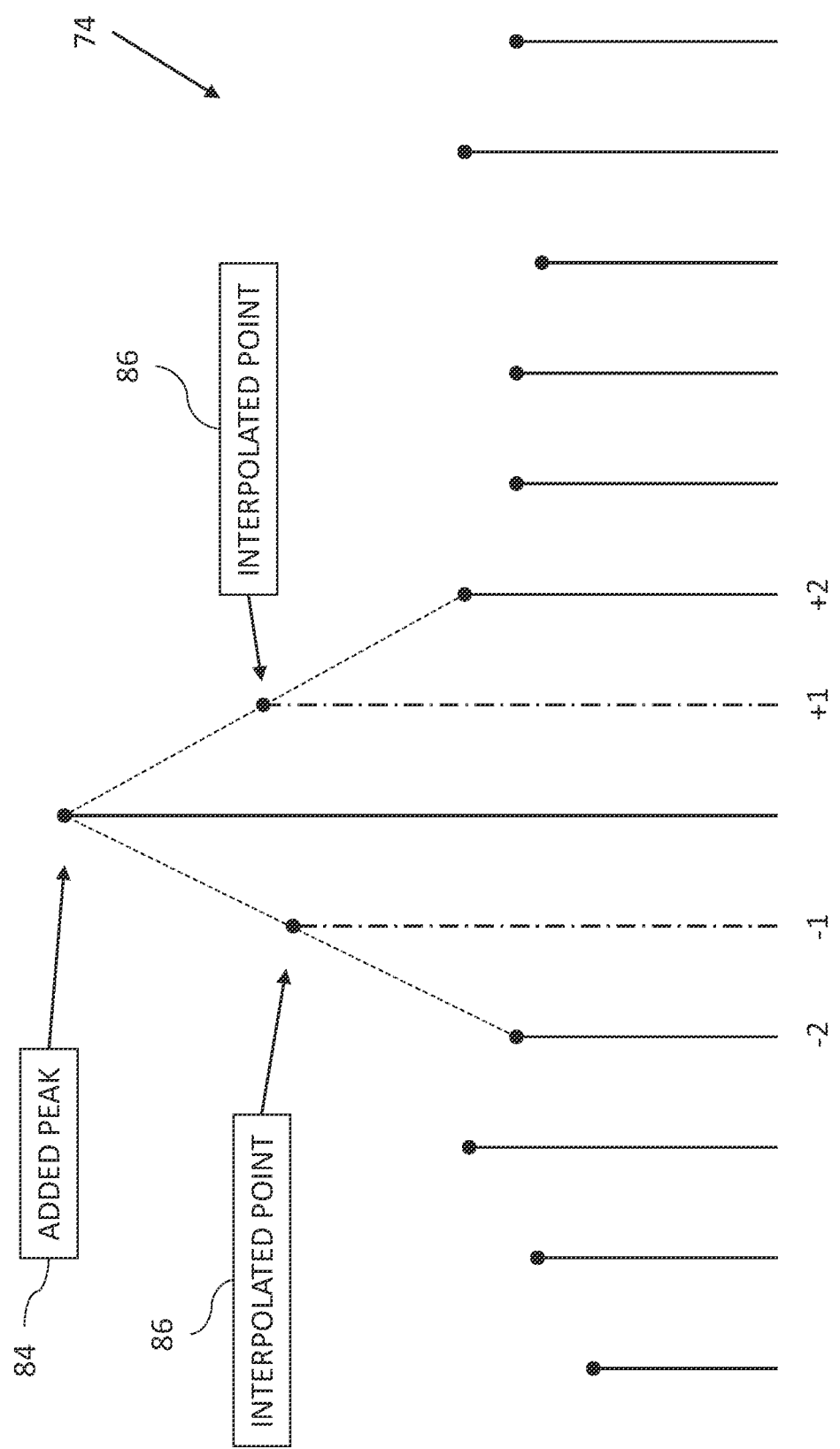
FIGS. 9 and 10 are examples of more aggressively filtered position signals with peak preservation in the system of FIG. 1.
Figure 10:
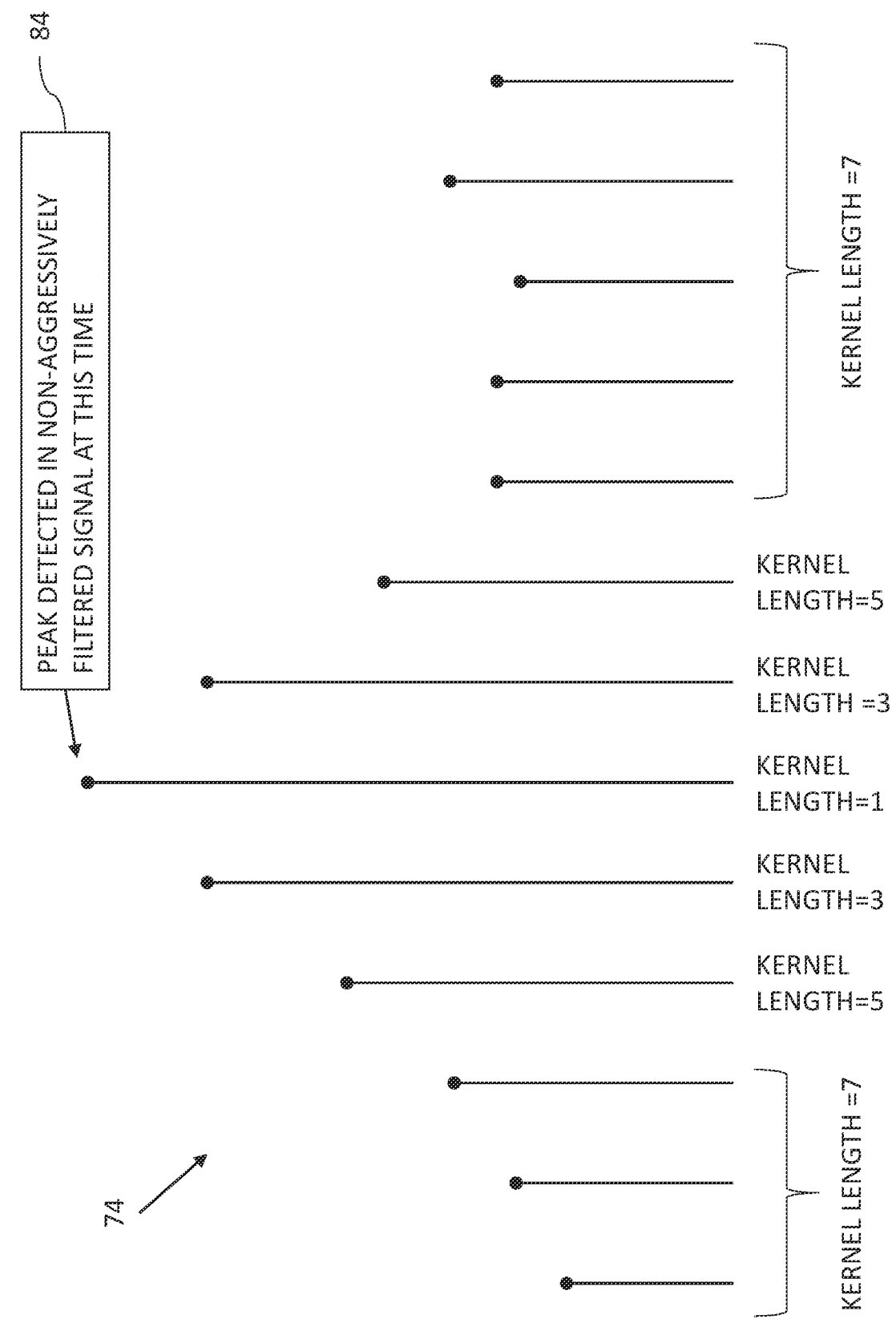

Reference is now made to FIGS. 9 and 10, which are examples of more aggressively filtered position signals with peak preservation in the system 20 of FIG. 1.

FIG. 9 shows that the peak 84 detected in the non-aggressively filtered position signal 68 of FIG. 8 has been copied to the aggressively filtered position signal 74 of FIG. 9. The amplitudes of the aggressively filtered position signal 74 around the added peak 84 at neighboring samples +1 and −1 from the peak 84 are interpolated (interpolated points 86) between the amplitude of the peak 84 and the amplitudes of the aggressively filtered position signal 74 at neighboring samples +2 and −2 (existing points 88). The interpolation can be performed on any suitable number of neighboring samples to give a smooth transitional effect. Any suitable interpolation algorithm, such as linear, polynomial or spline interpolation can be used. The example in FIG. 9 illustrates a linear interpolation.

FIG. 10 shows that the aggressively filtered position signal 74 is provided using the finite impulse response filter 76 of FIG. 2. Although the kernel length used by the finite impulse response filter 76 is longer than the finite impulse response filter 70 of FIG. 2, the kernel length used by the finite impulse response filter 76 is gradually reduced when approaching (from one direction, e.g., the direction of increasing time) the respective locations of the detected peaks 84 found in the non-aggressively filtered position signal(s) 68, up to some minimum kernel length at the location of the peak. The kernel length is then gradually increased when continuing away from the respective locations of the detected peaks 84, up to the original value of the kernel length. In the example of FIG. 10, the general length of the kernel used is 7. However, around the peak 84 detected by the non-aggressive filter, the kernel length of the finite impulse response filter 76 is reduced gradually from 7 to 5 (at positions +/−2 from the detected peak), then to 3 (at positions +/−1 from the detected peak), then to 1 (at the detected peak). A kernel length of 1 practically means copying the raw sample as-is. Gradually changing the kernel length results in a smoother transition between detected peaks and the rest of the aggressively filtered position signal 74. In the example of FIG. 10, the minimum kernel length at the detected peak locations is chosen as 1. In some embodiments, the minimum kernel length at the location of the peak may be set to be the same as the kernel length of the non-aggressive filter. This ensures that the peak value at the two signals is the same. For example, if the kernel length of the aggressive filter is 60, and the kernel length of the non-aggressive filter is 20, and if it is required to create a smooth transition effect in +/−3 samples around the peaks, the kernel length of the aggressive filter, which is generally 60, may be adjusted as {50, 40, 30, 20, 30, 40, 50} around the peaks. In this specific example, the adjusted kernel length of 20 coincides with the location of the peak. The transition effect obtained with this method is more accurate than the transition obtained with the interpolation method described in FIG. 9.

Figure 11:
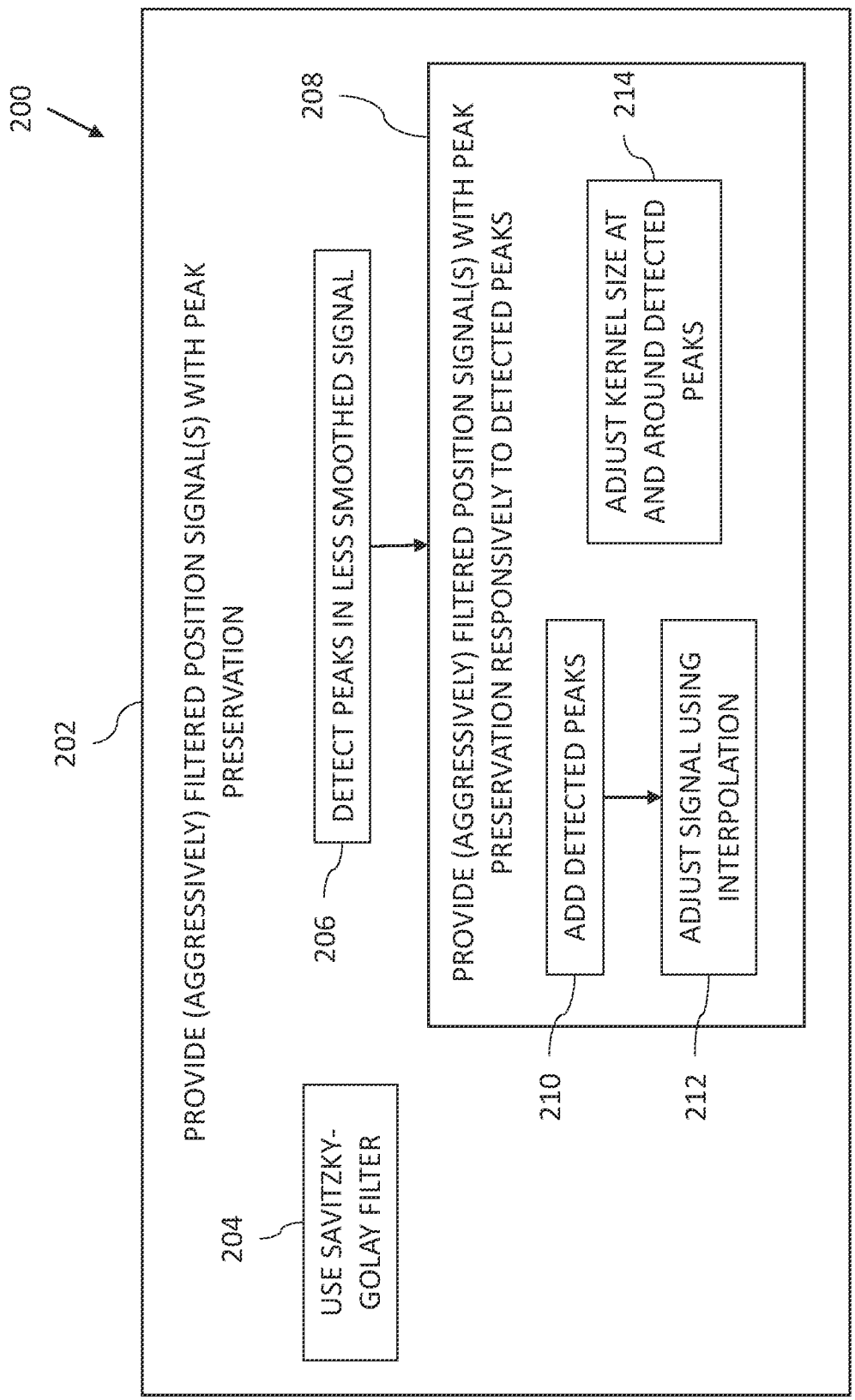
FIG. 11 is a flowchart including steps in a method of filtering with peak preservation in the system of FIG. 1.

Reference is now made to FIG. 11, which is a flowchart 200 including steps in a method of filtering with peak preservation in the system 20 of FIG. 1.

The smoothing filter 66 is configured to provide (block 202) the aggressively filtered position signal(s) 74 while at least partially preserving peaks 84 included in unfiltered signal(s) (e.g., position signal(s) 62) input into the smoothing filter 66 but would be excluded from the aggressively filtered position signal(s) 74 according to the second filtering level.

The step of block 202 may include smoothing filter 66 being configured to provide the aggressively filtered position signal(s) 74 responsively to a suitably configured Savitzky-Golay filter (block 204). For example, a Savitzky-Golay filter with a polynomial order of 5 and a frame length of 15 may preserve the peaks better than an FIR filter designed with equiripple, least squares or window methods.

In some embodiments, the smoothing filter 66 is configured to: detect (block 206) the peaks 84 in signal(s) (e.g., non-aggressively filtered position signal(s) 68 or in the position signal(s) 62) smoothed less than the aggressively filtered position signal(s) 74; and provide (block 208) the aggressively filtered position signal(s) 74 while at least partially preserving the peaks 84, included in the unfiltered input signal(s) but would be excluded from the aggressively filtered position signal(s) 74 according to the second filtering level, responsively to the detected peaks 84. The step of block 208 may include sub-steps of blocks 210 and 212, or the sub-step of block 214, described below.

In some embodiments, the smoothing filter 66 is configured to: add (block 210) the detected peaks 84 to the aggressively filtered position signal(s) 74; and adjust (block 212) the aggressively filtered position signal(s) 74 around the added peaks 84 responsively to interpolating between the added peaks 84 and the aggressively filtered position signal(s) 74 as described above in more detail with reference to FIG. 9.

In some embodiments, the finite impulse response filter 76 of the smoothing filter 66 is configured to provide the aggressively filtered position signal(s) 74 while at least partially preserving the peaks 84 (included in the unfiltered signal(s) input into the smoothing filter 66 but would be excluded from the aggressively filtered position signal(s) 74 according to the second filtering level). The preservation of peaks is performed by selecting the kernel of the finite impulse response filter 76 to be (gradually) reduced at and around the peak 84 as described in more detail above with reference to FIG. 10. The smoothing filter 66 is configured to apply (block 214) the second filtering level defined by the second kernel length, which is longer than the first kernel length, to first sections (away from the peaks 84) of the aggressively filtered position signal(s) 74, while applying at least one third filtering level defined by at least one third kernel length to second sections (at and around the peaks 84) of the aggressively filtered position signal(s) 74. The third kernel length(s) are shorter than the second kernel length and therefore provide less filtering and preserve the peaks. The second sections are selected to include regions of the detected peaks 84 and regions within a threshold around the detected peaks 84 as described in more detail with reference to FIG. 10.

In some embodiments, the smoothing filter 66 is configured to gradually reduce the third kernel length from an original value down to a given minimum value when approaching respective locations of the detected peaks 84, and gradually increase the third kernel length up to the original value when continuing away from the respective locations of the detected peaks 84.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A system comprising:
a catheter configured to be inserted into a body part of a living subject, and comprising a distal end;
at least one position sensor configured to provide at least one position signal indicative of a position of the distal end of the catheter over time;
a display;
a first smoothing filter configured to provide at least one first filtered position signal responsively to the at least one position signal and a first filtering level;
a second smoothing filter configured to provide at least one second filtered position signal responsively to the at least one position signal and a second filtering level, wherein the second filtering level provides more smoothing than the first filtering level; and
processing circuitry configured to:
find first data for position coordinates of the distal end responsively to the at least one first filtered position signal;
find second data for position coordinates of the distal end responsively to the at least one second filtered position signal,
using second data for position coordinates of the distal end to generate, and render to the display, an anatomical map of the body part responsively to the second data for position coordinates of the distal end; and
using first data for position coordinates of the distal end to render a representation of the distal end of the catheter to the display while showing movement of the distal end of the catheter responsively to the first data for position coordinates,
wherein the second smoothing filter is configured to:
provide the at least one second filtered position signal while at least partially preserving peaks included in at least one unfiltered signal input into the second smoothing filter but would be excluded from the at least one second filtered position signal according to the second filtering level,
detect the peaks in at least one signal smoothed less than the at least one second filtered position signal; and
provide the at least one second filtered position signal while at least partially preserving the peaks, included in the at least one unfiltered input signal but would be excluded from the at least one second filtered position signal according to the second filtering level, responsively to the detected peaks, and
add the detected peaks to the at least one second filtered position signal.

2. The system according to claim 1, wherein:
the first smoothing filter is configured to filter the at least one position signal responsively to the first filtering level providing the at least one first filtered position signal; and
the second smoothing filter is configured to filter the at least one position signal responsively to the second filtering level providing the at least one second filtered position signal.

3. The system according to claim 1, wherein:
the processing circuitry is configured to: compute position coordinates of the distal end responsively to the at least one position signal; and generate at least one position coordinate signal responsively to the computed position coordinates;
the first smoothing filter is configured to filter the at least one position coordinate signal responsively to the first filtering level providing the at least one first filtered position signal; and
the second smoothing filter is configured to filter the at least one position coordinate signal responsively to the second filtering level providing the at least one second filtered position signal.

4. The system according to claim 1, wherein the processing circuitry is configured to render the representation of distal end of the catheter and the anatomical map while showing movement of the catheter in the anatomical map.

5. The system according to claim 1, wherein the processing circuitry is configured to receive a user selected value and set the first filtering level responsively to the user selected value.

6. The system according to claim 1, wherein:
the first smoothing filter includes a first finite impulse response filter configured to provide the at least one first filtered position signal responsively to the at least one position signal and the first filtering level defined by a first kernel length; and
the second smoothing filter includes a second finite impulse response filter configured to provide the at least one second filtered position signal responsively to the at least one position signal and the second filtering level defined by a second kernel length, which is longer than the first kernel length.

7. The system according to claim 1, wherein the second smoothing filter is configured to provide the at least one second filtered position signal responsively to a Savitzky-Golay filter.

8. The system according to claim 1, wherein the second smoothing filter is configured to adjust the at least one second filtered position signal around the added peaks responsively to interpolating between the added peaks and the at least one second filtered position signal.

9. The system according to claim 1, wherein:
the first smoothing filter includes a first finite impulse response filter configured to provide the at least one first filtered position signal responsively to the at least one position signal and the first filtering level defined by a first kernel length; and
the second smoothing filter includes a second finite impulse response filter configured to provide the at least one second filtered position signal while at least partially preserving the peaks included in the at least one unfiltered signal input into the second smoothing filter but would be excluded from the at least one second filtered position signal according to the second filtering level, the second finite impulse filter being configured to apply the second filtering level defined by a second kernel length, which is longer than the first kernel length, to first sections of the at least one unfiltered signal, while applying at least one third filtering level defined by at least one third kernel length to second sections of the at least one unfiltered signal, the at least one third kernel length being shorter than the second kernel length, the second sections being selected to include regions of the detected peaks and regions within a threshold around the detected peaks.

10. The system according to claim 9, wherein the second smoothing filter is configured to gradually reduce the at least one third kernel length from an original value down to a given minimum value when approaching respective locations of the detected peaks, and gradually increase the at least one third kernel length up to the original value when continuing away from the respective locations of the detected peaks.

11. A method, comprising:
providing at least one position signal indicative of a position over time of a distal end of a catheter inserted into a body part of a living subject;
providing at least one first filtered position signal responsively to the at least one position signal and a first filtering level;
providing at least one second filtered position signal responsively to the at least one position signal and a second filtering level, wherein the second filtering level provides more smoothing than the first filtering level; and
finding first data for position coordinates of the distal end responsively to the at least one first filtered position signal;
finding second data for position coordinates of the distal end responsively to the at least one second filtered position signal;
using second data for position coordinates of the distal end to generate, and render to a display, an anatomical map of the body part responsively to the second data for position coordinates of the distal end; and
using first data for position coordinates of the distal end to render a representation of the distal end of the catheter to the display while showing movement of the distal end of the catheter responsively to the first data for position coordinates,
wherein the providing the at least one second filtered position signal includes providing the at least one second filtered position signal while at least partially preserving peaks included in at least one unfiltered input signal but would be excluded from the at least one second filtered position signal according to the second filtering level,
the method further comprising:
detecting the peaks in at least one signal smoothed less than the at least one second filtered position signal, and wherein the providing the at least one second filtered position signal includes providing the at least one second filtered position signal while at least partially preserving the peaks, included in the at least one unfiltered input signal but would be excluded from the at least one second filtered position signal according to the second filtering level, responsively to the detected peaks, and
adding the detected peaks to the at least one second filtered position signal.

12. The method according to claim 11, further comprising:
filtering the at least one position signal responsively to the first filtering level providing the at least one first filtered position signal; and
filtering the at least one position signal responsively to the second filtering level providing the at least one second filtered position signal.

13. The method according to claim 11, further comprising:
computing position coordinates of the distal end responsively to the at least one position signal;
generating at least one position coordinate signal responsively to the computed position coordinates;
filtering the at least one position coordinate signal responsively to the first filtering level providing the at least one first filtered position signal; and filtering the at least one position coordinate signal responsively to the second filtering level providing the at least one second filtered position signal.

14. The method according to claim 11, further comprising rendering the representation of distal end of the catheter and the anatomical map while showing movement of the catheter in the anatomical map.

15. The method according to claim 11, further comprising:
receiving a user selected value; and
setting the first filtering level responsively to the user selected value.

16. The method according to claim 11, wherein:
the providing the at least one first filtered position signal is performed by a first finite impulse response filter responsively to the at least one position signal and the first filtering level defined by a first kernel length; and
the providing the at least one second filtered position signal is performed by a second finite impulse response filter responsively to the at least one position signal and the second filtering level defined by a second kernel length, which is longer than the first kernel length.

17. The method according to claim 11, wherein the providing the at least one second filtered position signal includes providing the at least one second filtered position signal responsively to a Savitzky-Golay filter.

18. The method according to claim 11, further comprising adjusting the at least one second filtered position signal around the added peaks responsively to interpolating between the added peaks and the at least one second filtered position signal.

19. The method according to claim 11, wherein:
the providing the at least one first filtered position signal is performed by a first finite impulse response filter responsively to the at least one position signal and the first filtering level defined by a first kernel length; and
the providing the at least one second filtered position signal includes a second finite impulse response filter providing the at least one second filtered position signal while at least partially preserving peaks included in at least one unfiltered input signal but would be excluded from the at least one second filtered position signal according to the second filtering level, the method further comprising the second finite impulse filter applying the second filtering level defined by a second kernel length, which is longer than the first kernel length, to first sections of the at least one unfiltered signal, while applying at least one third filtering level defined by at least one third kernel length to second sections of the at least one unfiltered signal, the at least one third kernel length being shorter than the second kernel length, the second sections being selected to include regions of the detected peaks and regions within a threshold around the detected peaks.

20. The method according to claim 19, further comprising:
gradually reducing the at least one third kernel length from an original value down to a given minimum value when approaching respective locations of the detected peaks; and
gradually increasing the at least one third kernel length up to the original value when continuing away from the respective locations of the detected peaks.

21. A software product, comprising a non-transient computer-readable medium in which program instructions are stored, which instructions, when read by a central processing unit (CPU), cause the CPU to:

provide at least one first filtered position signal responsively to at least one position signal indicative of a position over time of a distal end of a catheter inserted into a body part of a living subject and a first filtering level;

provide at least one second filtered position signal responsively to the at least one position signal and a second filtering level, wherein the second filtering level provides more smoothing than the first filtering level; and find first data for position coordinates of the distal end responsively to the at least one first filtered position signal;

find second data for position coordinates of the distal end responsively to the at least one second filtered position signal;

using second data for position coordinates of the distal end to generate, and render to a display, an anatomical map of the body part responsively to the second data for position coordinates of the distal end; and using first data for position coordinates of the distal end to render a representation of the distal end of the catheter to the display while showing movement of the distal end of the catheter responsively to the first data for position coordinates, wherein the CPU provides the at least one second filtered position signal by providing the at least one second filtered position signal while at least partially preserving peaks included in at least one unfiltered input signal but would be excluded from the at least one second filtered position signal according to the second filtering level, the CPU further detects the peaks in at least one signal smoothed less than the at least one second filtered position signal, and wherein the providing the at least one second filtered position signal includes providing the at least one second filtered position signal while at least partially preserving the peaks, included in the at least one unfiltered input signal but would be excluded from the at least one second filtered position signal according to the second filtering level, responsively to the detected peaks, and the CPU further adds the detected peaks to the at least one second filtered position signal.

* * * * *